United States Patent [19]

Barrett

[11] Patent Number: 4,808,182

[45] Date of Patent: Feb. 28, 1989

[54] DESWELLED, HYDROGEL INTRAOCULAR LENSES

[75] Inventor: Graham D. Barrett, City Beach, Australia

[73] Assignee: Nestle, S.A., Vevey, Switzerland

[21] Appl. No.: 935,413

[22] Filed: Nov. 26, 1986

[51] Int. Cl.[4] .......................... A61F 2/16; B65D 81/22
[52] U.S. Cl. ........................................ 623/6; 206/5.1; 206/438
[58] Field of Search ...................... 623/6; 206/5.1, 210, 206/438, 439

[56] References Cited

U.S. PATENT DOCUMENTS

| | | | |
|---|---|---|---|
| 3,220,960 | 11/1965 | Wichterle et al. | 260/1.5 |
| 4,449,257 | 5/1984 | Koeniger | 623/6 |
| 4,556,998 | 12/1985 | Siepser | 623/6 |
| 4,573,998 | 3/1986 | Mazzocco | 623/6 |

FOREIGN PATENT DOCUMENTS

| | | |
|---|---|---|
| 0136807 | 4/1985 | European Pat. Off. . |
| 0166051 | 1/1986 | European Pat. Off. ................ 623/6 |
| WO85/00965 | 3/1985 | PCT Int'l Appl. ..................... 623/6 |

OTHER PUBLICATIONS

Barrett et al., "Corneal Endothelial Loss with New Intraocular Lenses", *Am. J. of Ophthalmology*, vol. 98, pp. 157–165 (1984).

Blumenthal et al., "Interaction of Soft and Hard Intraocular Lenses with Cat Cornea Endothelium", *Cornea*, vol. 1, pp. 129–132 (1982).

Epstein et al., *"Soft Implant Lenses in Cataract Surgery"*, Slack Incorporated, pp. 143–150 (1986).

*Encyclopedia of Polymer Science and Technology*, vol. 15, pp. 273–290 (1971).

*Primary Examiner*—Ronald L. Frinks
*Attorney, Agent, or Firm*—James A. Arno; Gregg C. Brown

[57] ABSTRACT

A method for reducing the size of hydrogel intraocular lenses by means of deswelling in hyperosmotic solutions (e.g., saturated sodium chloride solution) and a corresponding packaging arrangement are described. The deswelled, hydrogel lenses can be inserted through a much smaller surgical incision than fully hydrated lenses, yet retain all of the inherent advantages of hydrogel intraocular lenses (e.g., autoclavability). The lenses are rehydrated by the aqueous humor following implantation.

8 Claims, No Drawings

DESWELLED, HYDROGEL INTRAOCULAR LENSES

BACKGROUND OF THE INVENTION

1. Field of the Invention

The present invention relates to the field of artificial intraocular lenses suitable for replacement of the natural crystalline lenses in human eyes by means of surgical implantation. More particularly, this invention relates to intraocular lenses made from hydrogels which are shrunk temporarily prior to surgical implantation, thereby allowing a smaller incision to be utilized.

2. Discussion of Related Art

There have been many advances in surgical techniques and lens designs since the first implantation of an intraocular lens made from polymethylmethacrylate (PMMA) in 1949. Two of the recent, major advances are the use of phacoemulsification as a surgical technique for removing the natural crystalline lens from the eye and the introduction of materials other than PMMA for use in making intraocular lenses.

Phacoemulsification is an extracapsular technique that uses ultrasonic energy to fragment the natural crystalline lens into small particles. These small pieces are then removed by suction. One of the major advantages of this technique is that a small incision of only about 3 mm is required to remove the natural crystalline lens from the eye. This compares to incisions on the order of 11 mm when other surgical techniques are employed. When traditional, hard intraocular lenses made from PMMA are implanted, the incision must then be opened up to at least about 7 mm to allow insertion of the intraocular lens. This is viewed as a major drawback associated with the use of PMMA intraocular lenses, since surgeons would prefer to maintain the incision as small as possible.

There are other disadvantages associated with the use of PMMA in intraocular lenses. For example, such intraocular lenses cannot be autoclaved, but rather are usually made sterile by treatment with ethylene oxide which is a much less preferable treatment than autoclaving. Furthermore, there is increasing evidence that intraocular lenses made from PMMA can cause irreversible damage to endothelial cells. The above-discussed problems in connection with the use of PMMA in intraocular lenses have lead to the search for new materials which are suitable for use in intraocular lenses.

Hydrogels are ideal candidates for use in intraocular lenses since these materials have excellent biocompatibility and transparency, are autoclavable, have suitable mechanical properties and adaptable processing characteristics, and are inherently soft. Furthermore, it has been demonstrated that a hydrogel will cause very little endothelial cell damage, especially when compared to PMMA (Barrett, et al., *American Journal of Ophthalmology*, Vol. 98, pages 157-165 (1984)). Intraocular lenses made of a hydrogel have been described by Barrett in EP No. 136,807, by Wichterle in EP No. 166,051, by Koeniger in U.S. Pat. No. 4,449,257, by Mazzocco in U.S. Pat. No. 4,573,998, and by Blumenthal, et al., in *Cornea*, Vol. 1, pages 129-132 (1982). Typically these are hydrogels based on those described by Wichterle, et al., in U.S. Pat. No. 3,220,960. A comprehensive discussion of hydrogel intraocular lenses, including a discussion of the advantages of these lenses, is presented in the following text: *Soft Implant Lenses In Cataract Surgery*, Epstein, et al., Slack Incorporated, Thorofare, N.J. (1986). Reference is made to the above-cited publications for further background regarding the use of hydrogels in intraocular lenses. The contents of these publications are expressly incorporated herein by reference.

Hydrogels have several advantages when compared to polymethylmethacrylate as an intraocular lens material. The principal advantages are an ability to be autoclaved, a very significant reduction in endothelial cell damage and an ability to be brought to a higher level of purity. Other potential advantages include better biocompatibility and permeability, glare reduction, and physical adaptability to the internal environment of the human eye.

A further, very significant advantage associated with the use of hydrogels to make intraocular lenses is the flexibility and resilience of these materials. This flexibility and resilience provides the intraocular lenses with a capability to be inserted through a smaller incision than a polymethylmethacrylate intraocular lens by means of folding or other forms of manipulation, as described, for example, in U.S. Pat. No. 4,573,998, issued to Mazzocco. Another manner in which the size of a hydrogel lens can be reduced is by dehydrating the lens by some means and then allowing the lens to expand, in situ, via rehydration by the aqueous humor normally present in the eye. The latter method of reducing the size of the hydrogel lens can be accomplished by dehydrating the hydrogel and thereby reducing its size, inserting the intraocular lens in its reduced dimensions through a small incision and allowing the hydrogel intraocular lens to expand, in situ, to its normal equilibrium state via rehydration by the aqueous humor. This technique is based on the principle that hydrogels will take up water to an equilibrium point.

The dehydration/rehydration technique is proposed by Siepser in U.S. Pat. No. 4,556,998, as an improved method for the surgical implantation of hydrogel intraocular lenses, and is also mentioned in U.S. Pat. No. 4,573,998 (Mazzocco). Siepser describes the implantation of a hydrogel intraocular lens in its dehydrated state and its subsequent expansion via hydration by the natural fluid present in the eye; related approaches are described in U.S. Pat. No. 4,449,257 (Koeniger), and by Siepser and Epstein in respective chapters of the above-cited text titled "*Soft Implant Lenses In Cataract Surgery*". The approach described by Epstein concerns the insertion of hydrogel lenses which are either dehydrated, or partially hydrated by wetting a portion of the lenses prior to insertion. Epstein indicates that insertion of dry hydrogels can cause damage to the endothelium.

In the sole Example of U.S. Pat. No. 4,556,998, Siepser describes the implantation of an intraocular lens manufactured from a commercially available, dehydrated hydrogel that is sold under the tradename of HYDRON (manufactured by International Hydron). Siepser also describes the preparation of a hydrogel intraocular lens and subsequent dehydration of this lens via a freeze drying technique. Both of these approaches have a major disadvantage: dehydrated hydrogels cannot be sterilized by means of autoclaving. Since the autoclavability of hydrogels is a principal advantage associated with the use of hydrogels in intraocular lenses, this is a very serious disadvantage. Another disadvantage is that the implantation of dehydrated hydrogel lenses may also result in damage to the corneal endothelium, if there is contact between the lens and the endothelium. A still further disadvantage of implanting dehydrated hydrogel lenses is that a significant amount of time is required for the lenses to become hydrated following implantation. The Siepser patent indicates that from about 1 to about 24 hours or longer is required for full hydration. This is a serious disadvantage, since it frequently will not be possible to determine if a lens is properly positioned until it is fully hydrated and consequently fully expanded. Thus, it may be necessary to prolong a surgical procedure until a dehydrated lens becomes fully hydrated in situ.

It can thus be seen that while hydrogels are very viable candidates for use as an intraocular lens material, there is significant room for improvement in their surgical use as a replacement for the natural crystalline lens of the human eye. There is a real and continuing need for a method that will utilize the advantageous properties of hydrogels in a manner such that an intraocular lens can be delivered to the surgeon in a sterile state achieved by autoclaving, be inserted through a small incision, and swell rapidly following implantation. A primary object of this invention is to fill this need.

It is a more specific objective of this invention to treat a hydrogel intraocular lens in such a fashion as to maintain the lens in a state whereby it can be inserted through a small incision and rapidly expand when brought into contact with the natural fluids of the eye.

It is another specific objective of this invention to present to the ophthalmic surgeon a hydrogel intraocular lens that is capable of expanding rapidly after insertion and is available in a sterile state achieved by autoclaving.

The foregoing objectives and other general objectives of the present invention are achieved by deswelling a hydrated, hydrogel intraocular lens in a physiologically acceptable, hyperosmotic solution, autoclaving the deswelled lens and storing the deswelled, sterilized lens in the hyperosmotic solution.

The present invention will be more completely understood following review of the detailed description of the invention which follows.

SUMMARY OF THE INVENTION

An improved system for the implantation of intraocular lenses made from hydrogels is provided. The method involves the storage of a hydrogel intraocular lens in a hyperosmotic, physiologically acceptable solution that will deswell the hydrogel intraocular lens, thus reducing the size of the lens, particularly the diameter of the lens. As constituted, this combination of physiologically acceptable aqueous solution and hydrogel intraocular lens may be sterilized by autoclaving, stored in the normal manner and delivered to the surgeon in a sterile state. Thus, the surgeon has available a hydrogel intraocular lens of reduced size that is advantageous in that a smaller incision will be required, and has a lens which has had its sterility ensured by means of autoclaving.

DETAILED DESCRIPTION OF PREFERRED EMBODIMENTS

Various types of hydrogels may be utilized in the present invention. Specific examples of suitable types of hydrogels include polyhydroxyethylmethacrylate and related hydrogels described in U.S. Pat. No. 3,220,960, issued to Wichterle, et al. There are numerous other types of hydrogels which might find use in the present invention, including the following types:

poly (NVP-co-MMA),
poly (HEMA-co-NVP),
poly (NVP-g-HEMA),
poly (glyceryl methacrylate-co-MMA),
copolymers based on N-(1,1-dimethyl-3-oxobutyl acrylamide),
copolymers based on N,N-dimethyl-acrylamide,
copolymers based on hydrolyzed acrylonitrile units,
copolymers based on HEMA and 2-ethoxyethyl methacrylate,
copolymers based on methyl methacrylate and acrylic acid,
copolymers based on glycidyl methacrylate,
copolymers based on allyl 2-hydroxyethyl ether,
copolymers based on vinyl acetate and HEMA, and
collagen and modified collagen.

Poly HEMA and poly (NVP-co-MMA) are two types of preferred hydrogels.

Hydrogels have many unique properties. One of the most important of these unique properties is the equilibrium water content of hydrogels. Many of the other important properties of hydrogels are directly related to equilibrium water content. The equilibrium water content of a hydrogel can be altered by various environmental factors. Specific parameters such as osmolarity, pH and temperature are known to affect the equilibrium water content of a hydrogel.

It has long been known that different solvents and changes in osmolarity can strongly influence the equilibrium water content of hydrogels. A detailed discussion of these and other factors affecting equilibrium water content is set forth in the *Encyclopedia of Polymer Science and Technology*, Vol. 15, pages 273-290 (1971). Changes in equilibrium water content will result in swelling-deswelling phenomena.

These swelling-deswelling phenomena have been explained in thermodynamic terms involving osmotic forces and chemical potential. Solutes will lower the chemical potential of water. If the chemical potential of water in an aqueous solution in contact with a hydrogel is lower than the chemical potential of the water inside the hydrogel, the hydrogel will deswell. If, on the other hand, the chemical potential of the water in the hydrogel is lower than that of the outside solution, the hydrogel will swell. At equilibrium, the chemical potentials of water inside and water outside the hydrogel are equal.

The present invention is based on the use of the principles of swelling and deswelling in a unique manner to deswell hydrogels (reduce the size) and thus accomplish the deswelling of a hydrogel intraocular lens, whereby an intraocular lens that can be sterilized by autoclaving and inserted by a surgeon through a reduced incision is provided.

The hydrogel intraocular lenses of the present invention are deswelled by means of hyperosmotic, physiologically acceptable solutions. For sake of convenience, these solutions are referred to herein as being "hyperosmotic." It should be noted, however, that the phenomena of swelling-deswelling are influenced not only by osmotic forces, but also by chemical potential, and other thermodynamic and chemical phenomena, as pointed out above.

The deswelling achieved by means of the present invention will not result in total dehydration of a hydrated, hydrogel intraocular lens. Rather, the deswelling method of the present invention will result in a reduction in the water content of the hydrogel sufficient to significantly reduce the size of the lens. In general, a size reduction of approximately 10% or more is considered significant. A reduction in size is generally equated with a reduction in the diameter or surface area of a lens. In order to achieve a significant reduction in the size of a hydrogel lens, it will typically be necessary to reduce the water content of the hydrated hydrogel by several percent. However, the water content of the hydrogel will never be reduced to a point of dehydration or near dehydration (i.e., a water content of a few percent), and will generally not be reduced beyond a range of about 10% to 20%.

The fact that the deswelling process of the present invention does not result in total dehydration of hydrogel lenses represents a very important distinction between the deswelled lenses of the present invention and the dehydrated lenses described by Siepser and others, because it takes much longer to hydrate a dehydrated intraocular lens than to rehydrate an intraocular lens which has been deswelled in accordance with the present invention. As noted above, the Siepser patent indicates that a period of about 1 to 24 hours, or longer, is required to hydrate a dehydrated intraocular lens following implantation. In contrast, the deswelled hydrogel lenses of the present invention are normally rehydrated sufficiently to facilitate implantation within 30 minutes or less, and in most cases within 5 to 10 minutes or less. The apparent explanation for this significant difference between the time required for hydration of a dehydrated hydrogel intraocular lens and the time required for rehydration of a hydrated hydrogel intraocular lens which has been deswelled in accordance with the present invention concerns the initial water contents of the respective lenses. More particularly, a considerable amount of time is required to bring a totally dehydrated or "dry" hydrogel intraocular lens to a point at which its water content ranges from a few percent to roughly ten percent, for example. The deswelled hydrogel lenses of the present invention are not subject to this time consuming, initial hydration period, because the lenses are not completely dehydrated or "dry", but rather will generally have a water content of 10% or more. Consequently, the deswelled hydrogel lenses of the present invention reach hydration equilibrium much more rapidly than totally dehydrated hydrogel lenses. This represents a very significant advantage of the present invention.

The reduction in size that can be obtained with the deswelling method of the present invention is dependent on the type of hydrogel polymer being treated and the type of hyperosmotic solution utilized. For example, poly (HEMA-co-methacrylic acid) will deswell to a much greater extent than poly (HEMA) containing essentially no methacrylic acid, when similar deswelling conditions are used. In general, it would be expected that hydrogel polymers that contain ionic charges will deswell to a greater extent than hydrogel polymers that are essentially neutral. The degree of deswelling is also a function of the solute chosen and the concentration of the solute that is used. For example, with poly (hydroxyethyl methacrylate) equilibration with a saturated sodium chloride solution will result in a size reduction in the range of about 30%, while a 13% aqueous solution of glycerol results in a size reduction of about 6%. The use of a 6.5% sodium chloride solution with poly (hydroxyethyl methacrylate) will result in a size reduction of about 12%.

There are few restrictions on the choice of the solute to prepare the hyperosmotic solution. The solute must be physiologically acceptable and not react in an irreversible manner with the hydrogel polymer. It should also be chosen so that the time for swelling (rehydration) of the hydrogel intraocular lens to its original size or nearly its original size is at a minimum; a swelling time of 30 minutes or less is preferred, and a swelling time of about 5 minutes or less is particularly preferred. These swelling times represent the amount of time required for a deswelled lens to reswell to a point at which proper fixation of the lens in the eye is possible. The amount of time required for complete equilibration or reswelling of a deswelled hydrogel lens may be significantly longer than these periods in some instances.

A wide range of solutes will meet these requirements. Specific examples include inorganic salts such as sodium chloride, potassium chloride, calcium chloride, sodium sulfate, magnesium chloride, sodium acetate, and sodium citrate; and organic compounds such as glycerol, mannitol, and high molecular weight compounds or polymers such as dextran or viscoelastic substances such as chondroitin sulfate. A preferred solute is sodium chloride in a concentrated aqueous solution. A particularly preferred solute is a saturated sodium chloride solution.

An advantageous aspect of the use of saturated sodium chloride is the rapid nature of the deswelling-swelling equilibrations cycle. It has been found that deswelling essentially reaches an equilibrium state in less than one hour. However, most preferred is to allow equilibrations to be attained by standing overnight. The swelling equilibration (size increase) takes place in a similar manner. When placed in the eye, a deswelled hydrophilic intraocular lens will swell very rapidly and will approach equilibrium in less than 30 minutes. In most cases, the lens will have swelled sufficiently to facilitate fixation within 5 to 10 minutes or less. Therefore, fixation will take place in a relatively brief period of time.

Another advantageous aspect of using a saturated sodium chloride solution as the solute is the amount of size reduction obtained. For an essentially neutral hydrogel polymer such as polyhydroxyethylmethacrylate, a size reduction of about 30% may be obtained. For ionic hydrogel polymers such as poly (HEMA-co-methacrylic acid), a size reduction of about 50% may be obtained upon deswelling in a saturated sodium chloride solution. Even higher degrees of size reduction can be obtained with hydrogel polymers having higher water contents and/or more of an ionic nature.

As mentioned above, a significant advantage of using the method of the present invention to deswell hydrogel intraocular lenses is that the deswelled hydrogel intraocular lenses still contain water. As a result, the deswelled hydrogel intraocular lenses are still flexible. This flexibility allows the lenses to be folded. This is a very significant advantage over dehydrated hydrogel intraocular lenses; hydrogel intraocular lenses that are dehydrated (by evaporation) to a hard, dry state generally cannot be folded due to the brittleness of the dehydrated hydrogel polymer. For example, it has been discovered that poly (hydroxyethylmethacrylate) that is deswelled by being placed in a saturated sodium chloride solution for 90 minutes displays a size reduction of about 30%; the water content of the deswelled hydrogel was approximately 14% (measured gravimetrically). A deswelled hydrogel intraocular lens having these characteristics can be folded and inserted through an even smaller incision.

A further advantage of the deswelled hydrogel intraocular lenses of the present invention is that the surfaces of the lenses are wettable. This characteristic facilitates insertion of the lenses through an incision.

In accordance with another embodiment of the present invention, a fully hydrated hydrogel intraocular lens is first folded, and then placed in a hyperosmotic solution and deswelled. The solution and lens contained therein are then autoclaved, stored, and later delivered to the surgeon. The surgeon would then be able to remove the folded hydrogel intraocular lens from the sterile, physiological acceptable solution and insert the folded lens through a very small incision, perhaps as small as 2.5 to 4.0 mm.

The intraocular lenses of the present invention may be prepared and used as follows. A hydrogel polymer is first selected from any of the hydrogels known to be useful in intraocular lenses. An intraocular lens is then processed from the hydrogel polymer by methods known in the art, such as lathing and molding. The intraocular lens is then processed by known steps, including at least the steps of extraction and hydration. At this stage the intraocular lens is composed of a hydrogel having a defined equilibrium water content. The hydrogel intraocular lens is then placed into a convenient volume (about 0.5 mL to about 2 mL, depending on package design) of a hyperosmotic, physiologically acceptable solution that is in the container that will be used for storage and shipment. The deswelling (size reduction) reaches an equilibrium point in a brief period of time (i.e., 1 hour or less). However, standing overnight (i.e., approximately 16 hours) is preferred. At this point, the package containing the deswelled, hydrogel intraocular lens and hyperosmotic solution is autoclaved using standard conditions, such as those defined by the United States Food and Drug Administration. The sterile package can then be stored in inventory and when required shipped to a surgeon.

When the lens is required for implantation, the surgeon will open the sterile package and remove the hydrogel intraocular lens that is in its deswelled state (reduced size). The surgeon would directly implant the hydrogel intraocular lens using known techniques through an incision that would be smaller than that required for a hydrogel intraocular lens that had not been deswelled by a hyperosmotic solution. The lens could be inserted in a folded or normal state, depending on the preferences of the surgeon. Upon placement in the eye and contact with the aqueous humor, the deswelled hydrogel intraocular lens immediately begins to swell to a new increased equilibrium water content (and increased equilibrium size). After placement of the hydrogel intraocular lens the surgeon would complete the surgery using known, established techniques. The hydrogel intraocular lens will swell in the aqueous humor very rapidly, with equilibration being approached within approximately 30 minutes or less, and in most cases within 5 to 10 minutes or less. The degree of swelling which takes place within these time periods is sufficient to facilitate fixation of the lens in the eye; in some instances, complete equilibration may require several hours.

In accordance with another embodiment of the present invention, an ophthalmic surgeon may be supplied with a sterile hyperosmotic solution in one container and a sterile, hydrated, hydrogel lens in a separate container. Prior to surgery, the surgeon would deswell the hydrogel lens by placing it in the hyperosmotic solution for a few minutes. The deswelled lens would then be removed from the hyperosmotic solution and implanted. This approach provides the surgeon with some degree of control over the extent to which the hydrogel lens will be deswelled, and the associated amount of time required to rehydrate or reswell the lens following implantation.

Variations of the above-described steps for preparing and using the deswelled hydrogel intraocular lenses of the present invention will be readily apparent to those skilled in the art.

The invention will be further described in connection with the following examples which are given for purposes of illustration only and should not e construed as limiting the invention in any respect. It should be noted that some of the data regarding area reduction attributable to deswelling were obtained from experiments with hydrogel films rather than hydrogel intraocular lenses, due to the ease of measuring the change in size of a sample cut from a film. The results for films and intraocular lenses of the same chemical compositions are substantially equivalent.

EXAMPLE 1

Preparation of Poly (hydroxyethylmethacrylate)

A film of poly (hydroxyethylmethacrylate) was prepared by polymerization of purified hydroxyethylmethacrylate monomer between (4×4 inch) glass plates. The glass plates were treated with dimethyldichlorosilane and hydrolyzed to silanize the surface. Masking tape was placed around the edges of a glass plate to control the film thickness. The monomer was placed on a glass plate which was then secured to a second plate by means of metal clips, and the assembly was placed in an oven and heated at 60° C. for one and one-half hours. The glass plate assembly was then heated to 90° C. for an additional 30 minutes. The thin film was then removed from the glass plate assembly and stored in distilled water (phosphate buffer, pH 7.4). The water was changed several times to ensure complete extraction. The film was then stored in distilled water (phosphate buffer, pH 7.4) until required for experiments. US 245 (2,5-dimethyl-2,5-diperoxy-2'-ethylhexoate hexane) was used as the polymerization initiator.

The hydroxyethylmethacrylate monomer was purified by distillation and extraction to remove impurities such as ethylene glycol dimethacrylate and methacrylic acid. The monomer to be polymerized contained 0.3% ethylene glycol dimethacrylate and less than 0.05% methacrylic acid.

EXAMPLE 2

Deswelling of Poly HEMA by Saturated Sodium Chloride Solution

A film of poly HEMA hydrogel was prepared as in Example 1. Small squares (about 14×14 mm) were carefully cut from the film. The area was measured by placing the sample on a marked grid (1×1 mm markings) and noting the measurements under 2X magnification.

A saturated saline solution was prepared by dissolving reagent grade sodium chloride in distilled water. The approximate concentration was 27%. About 10 mL was placed into a flint glass vial with a two-piece plastic stopper.

The cut, measured samples of poly HEMA were placed into the vials, capped and allowed to stand for specified times. At the end of the specified time the sample was removed from the vial and its area measured in the same fashion. The results are shown in Table 1 below.

TABLE 1

Area Reduction Upon Deswelling
Poly HEMA With Saturated Sodium Chloride

| Time (min) | Initial Area (mm²) | Area After Deswelling (mm²) | % Area Reduction |
|---|---|---|---|
| 15 | 208 | 147 | 29 |
| 60 | 207 | 144 | 30 |

EXAMPLE 3

Comparison of Deswelling by Saturated Aqueous Sodium Chloride Solution and Concentrated Aqueous Sodium Chloride Solution Circular discs were cut from poly HEMA films prepared as in Example 1. A concentrated sodium chloride solution (6.5%) was prepared in distilled water. The procedures of Example 2 were used with the exception that the area change was calculated by measuring the change in the diameter of the circular discs. Three samples were used for each deswelling solution; the results reported in Table 2 below are averages of the three samples. The equilibration time was 90 minutes for each sample.

TABLE 2

Comparison of Deswelling by Saturated Sodium Chloride Solution and 6.5% Aqueous Sodium Chloride Solution

| Solutions | Initial Area (mm²) | Area After Deswelling (mm²) | % Area Reduction |
|---|---|---|---|
| Saturated | 254 | 191 | 25 |
| 6.5% | 254 | 216 | 15 |

EXAMPLE 4

Water Content of Deswelled Poly HEMA

A film of poly HEMA was prepared as in Example 1. Three samples were cut from the film, weighed (all in the range of 0.1 g) and placed in a saturated sodium chloride aqueous solution as in Example 2. After 90 minutes the samples were removed from the vials, reweighed and then dried to dryness by heating for 3 hours at 100° C. and 31 inches Hg vacuum. The average water content for the deswelled samples was 14%. The measured water content of a sample of the hydrogel film that was not deswelled was 36%.

EXAMPLE 5

Deswelling of Poly (HEMA-co-Methacrylic Acid) by Saturated Sodium Chloride Solution Films of a copolymer of HEMA (96% w/w) and methacrylic acid (4% w/w) were prepared as in Example 1. The deswelling and area measurement were carried out as in Example 2. The results of deswelling are shown in Table 3 below.

TABLE 3

Area Reduction Upon Deswelling of Poly (HEMA-co-methacrylic acid) With Saturated Sodium Chloride Solution

| Time (hr) | Initial Area (mm²) | Area After Deswelling (mm²) | % Area Reduction |
|---|---|---|---|
| ½ | 172 | 95 | 45% |
| 16 | 172 | 86 | 50% |

It can be seen that with this hydrogel the amount of deswelling (area reduction) is greater than with poly HEMA using the same deswelling conditions, i.e., compare the results of this example to those of Example 2.

EXAMPLE 6

Area Reduction Upon Deswelling of Poly (HEMA-co-Methacrylic) With an Aqueous Mannitol Solution Example 5 was repeated with the exception that the hyperosmotic solution was a 20% (w/v) aqueous solution of mannitol. The results of deswelling are shown in Table 4 below. The osmolarity of the mannitol solution was measured to be 1,550 mosM/kg.

TABLE 4

Area Reduction Upon Deswelling of (Poly HEMA-co-methacrylic acid) by a Hyperosmotic Aqueous Mannitol Solution

| Time | Initial Area (mm²) | Area After Deswelling (mm²) | % Area Reduction |
|---|---|---|---|
| ½ | 259 | 266 | 0 |
| 40 | 259 | 210 | 19% |

EXAMPLE 7

Deswelling of Hydrogel Intraocular Lenses With a Saturated Saline Solution

Two hydrogel intraocular lenses made from poly HEMA and having a configuration similar to the lenses described by Barrett in EP No. 136,807 were deswelled using the techniques described in Example 2 above. Based on measurements of the length and width of the lenses taken before and after the deswelling, the deswelling was determined to have reduced the area of the lenses by approximately twenty-four percent (24%).

EXAMPLE 8

Deswelling of Hydrogel Intraocular Lenses With Various Aqueous Salt Solutions

Intraocular lenses of the type described in Example 7 were deswelled with saturated aqueous solutions containing magnesium chloride, potassium chloride, sodium acetate, sodium citrate, and calcium chloride, respectively. Following equilibration in these solutions, the diameters of the deswelled lenses were measured to determine the reduction in area attributable to the deswelling. The results of these determinations are set forth in Table 5 below.

TABLE 5

Deswelling of Poly HEMA Lenses With Saturated Aqueous Salt Solutions

| Salt Solution | % Area Reduction |
|---|---|
| Magnesium Chloride | 30 |
| Potassium Chloride | 25 |
| Sodium Acetate | 38 |
| Sodium Citrate | 35 |

TABLE 5-continued

Deswelling of Poly HEMA Lenses
With Saturated Aqueous Salt Solutions

| Salt Solution | % Area Reduction |
| --- | --- |
| Calcium Chloride | 30 |

What is claimed is:

1. A method for reducing the area of a hydrogel intraocular lens so as to allow its implantation through a smaller incision than the incision which would normally be required for said lens, comprising deswelling the hydrogel intraocular lens by equilibration in a physiologically acceptable, hyperosmotic solution.

2. A method according to claim 1, wherein the hyperosmotic solution is selected from solutions containing sodium chloride, potassium chloride, calcium chloride, sodium sulfate, magnesium chloride, sodium acetate, sodium citrate, glycerol, mannitol, dextran, or chondroitin sulfate.

3. A deswelled, hydrogel intraocular lens prepared according to the method of claim 1.

4. A packaging arrangement for an intraocular lens, comprising:
a sealable container suitable for receiving a hydrogel intraocular lens, said container having sufficient strength to withstand autoclaving; a physiologically acceptable, hyperosmotic solution contained in said container; and a deswelled, hydrogel intraocular lens present in said solution.

5. A packaging arrangement according to claim 4, wherein the hyperosmotic solution is selected from solutions containing sodium chloride, potassium chloride, calcium chloride, sodium sulfate, magnesium chloride, sodium acetate, sodium citrate, glycerol, mannitol, dextran, or chondroitin sulfate.

6. A packaging arrangement according to claim 4, wherein the hyperosmotic solution and the deswelled, hydrogel intraocular lens have been sterilized by means of autoclaving.

7. A method of preparing a deswelled, hydrogel intraocular lens, comprising:
placing a physiologically acceptable hyperosmotic solution in a sealable container; submerging a hydrated, hydrogel intraocular lens in said solution; deswelling said hydrogel intraocular lens in said solution; and autoclaving said container and its contents to provide a sterilized package containing a sterilized, deswelled, hydrogel intraocular lens.

8. A method according to claim 7, wherein the hyperosmotic solution is selected from solutions containing sodium chloride, potassium chloride, calcium chloride, sodium sulfate, magnesium chloride, sodium acetate, sodium citrate, glycerol, mannitol, dextran, or chondroitin sulfate.

* * * * *